(12) United States Patent
Möller et al.

(10) Patent No.: US 6,333,327 B2
(45) Date of Patent: Dec. 25, 2001

(54) METHOD FOR THE TREATMENT OF MULTIPLE SCLEROSIS

(75) Inventors: Lennart Möller, Lästringevägen; Jan Bergman, Lekgränd, both of (SE)

(73) Assignee: Leif J. I. Lundblad, Stockholm (SE)

( * ) Notice: Subject to any disclaimer, the term of this patent is extended or adjusted under 35 U.S.C. 154(b) by 0 days.

(21) Appl. No.: 09/784,302

(22) Filed: Feb. 16, 2001

Related U.S. Application Data

(60) Provisional application No. 60/183,372, filed on Feb. 18, 2000.

(51) Int. Cl.$^7$ .................................................. A61K 31/495
(52) U.S. Cl. .............................................. 514/250
(58) Field of Search ............................................. 514/250

(56) References Cited

U.S. PATENT DOCUMENTS 4,990,510 * 2/1991 Bergman et al. ..................... 514/250

OTHER PUBLICATIONS

Ruuls et al., "The length of Treatment Determines Whether IFN–β Prevents or Aggravates Experimental Autoimmune Encephalomyelitis in Lewis Rats", *The Journal of Immunology,* (1996), vol. 157, pp. 5721–5731.

Van Der Meide et al., "Discontinuation of treatment with IFN–β leads to exacerbation of experimental autoimmune encephalomyelitis in Lewis rats. Rapid reversal of the antiproliferative activity of IFN–β and excessive expansion of autoreactive T cells as disease promoting mechanisms", *Journal of Neuroimmunology,* (1998), vol. 84, pp. 14–23.

Smith et al., "Autoimmune encephalomyelitis ameliorated by AMPA antagonists", *Nature Medicine,* (2000), vol. 6, No. 1, pp. 62–66.

* cited by examiner

*Primary Examiner*—Raymond Henley, III
(74) *Attorney, Agent, or Firm*—Browdy and Neimark

(57) ABSTRACT

Use of a compound of formula I

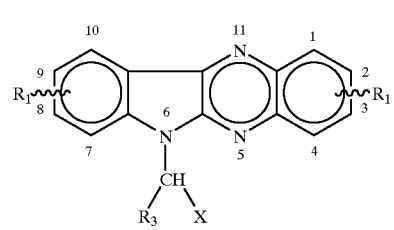

wherein $R_1$ represents hydrogen or one or several, preferably 1 to 4, similar or different substituents in the positions 1–4 and/or 7–10, selected from halogen, preferably Br, lower alkyl/alkoxy group having not more than 4 carbon atoms, trifluoromethyl group, trichloromethyl group; and in one of the positions 7–10 $R_1$ can be a hydroxyl group;

X is a group —$(CH_2)_n$—$R_2$, wherein $R_2$ represents a nitrogen containing basic residue such as $NH_2$, $NHR_4$ or $NR_5R_6$, wherein $R_4$, $R_5$ and $R_6$ independently are lower alkyl or cycloalkyl and n is an integer of from 1 to 4 and $R_3$ represents hydrogen, lower alkyl/cycloalkyl group having not more than 4 carbon atoms, and the physiologically acceptable addition products of the compounds with acids and halogen adducts, preferably adducts with iodine, iodine monochloride or iodine monobromide, for preparing a drug for treatment of MS (multiple sclerosis).

18 Claims, 4 Drawing Sheets

CLINICAL SCORE; DOUBLE BLIND EXAMINATION OF CLINICAL SYMPTOMS
IMMUNIZATION TAKES PLACE DAY 0
ADMINISTRATION OF THE DRUG EVERYDAY
OPEN TRIANGLES = INTERFERON-BETA
CROSSES = NEGATIVE CONTROL
OPEN CIRCLES = THE COMPOUND B220

METHOD FOR THE TREATMENT OF MULTIPLE SCLEROSIS

The present application claims the benefit of U.S. Provisional Application No. 60/183,372 file Feb. 18, 2000.

The present invention relates to the use of a compound of the general formula I

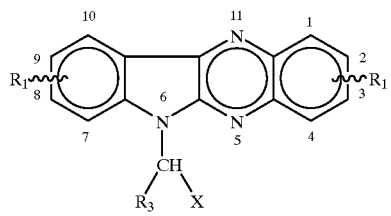

for preparing a drug for treatment of MS (multiple sclerosis).

MS is a chronic disease with its origin in the central nervous system (CNS) that often leads to severe consequences. MS can be mild with minor symptoms to severe paralysis and loss of vision. The diagnosis is most common between the ages of 20 to 40 and thereafter the disease continues the remaining life span. Sometimes MS develops rapidly, while in other cases the afflicted persons can live for many decades only with some disabilities.

MS is more frequent at northern latitudes. Depending on region in the western world the prevalence varies with 50–150 cases per 100,000. In the US only, some 250,000–350,000 have the MS diagnosis. Females have a double risk, compared to males, to develop MS.

It is generally accepted that the immune defense of a patient with MS attacks the CNS, while the exact mechanisms are unknown. Due to inflammation of the nerve isolation (myeline) there are dysfunctions and short-circuits of nerve fibers and thereby effects on the muscles controlled by these nerves.

The treatment of MS is focused on the reduction of symptoms. To cure or stop the MS disease is not possible with today's knowledge. Consequently there does not exist any drug to cure or delay onset of the disease. Treatments used are:

Transplantation of bone marrow and treatment of cytostatics and lifelong administration of immunosupressive drugs. This method could work for some patients but it is very expensive and includes several risks for the patient. Administration of cytostatics is still considered to be controversial in treatment of MS since the effects are unclear and potential side- effects are severe.

There are two drugs used with the aim to cure or delay the MS disease; Interferon-beta (trademarks Avonex® and Betaseron®) can reduce the symptoms among certain groups of patients and is therefore administered to most patients for ethical reasons. The effect is unclear for the population of MS patients and it is a very expensive treatment.

Glatiramer acetate (trademark Copaxone®) can for some patients reduce the frequence of attacks, but the side effects are substantial and there is a problem to distinguish the symptoms of the MS disease and side effects.

Today there does not exist an effective treatment for MS. The treatment is focused on reducing symptoms. Tests with transplantation and different drug treatments to cure the disease have so far not shown any solutions. It can work for some patients, although there are risks, side effects and very high costs involved. MS is a rather common disease that appears early in life. In addition it is a life long disease with severe symptoms. The demand for drugs that can protect the MS patients for the severe development of the disease is therefore of high priority.

According to the present invention it has surprisingly been found that a substituted indolo-quinoxaline of the following general formula I can be used for preparing a drug for treatment of MS.

The compound which according to the present invention is to be used for preparing a drug for treatment of MS is a compound of the following general formula I

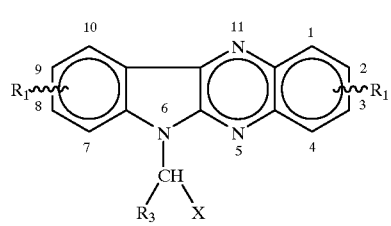

wherein $R_1$ represents hydrogen or one or several, preferably 1 to 4, similar or different substituents in the positions 1–4 and/or 7–10, selected from halogen, preferably Br, lower alkyl/alkoxy group having not more than 4 carbon atoms, trifluoromethyl group, trichloromethyl group; and in one of the positions 7–10 $R_1$ can be a hydroxyl group;

X is a group $—(CH_2)_n—R_2$, wherein $R_2$ represents a nitrogen containing basic residue such as $NH_2$, $NHR_4$ or $NR_5R_6$, wherein $R_4$, $R_5$ and $R_6$ independently are lower alkyl or cycloalkyl and n is an integer of from 1 to 4 and $R_3$ represents hydrogen, lower alkyl/cycloalkyl group having not more than 4 carbon atoms, and the physiologically acceptable addition products of the compounds with acids and halogen adducts, preferably adducts with iodine, iodine monochloride or iodine monobromide.

$R_1$ is preferably selected from hydrogen and lower alkyl groups, especially methyl. More preferably $R_1$ is methyl in positions 2 and 3 and hydrogen in the other positions.

Suitable compounds are such compounds wherein $R_1$ is hydroxy in one of the positions 7–10, especially in position 9.

The compounds used according to the present invention and their preparation are described in EP patent 0238459 and U.S. Pat. No. 4,990,510 which are incorporated herein by reference.

A compound which has proven to be especially effective is the compound of the following formula II

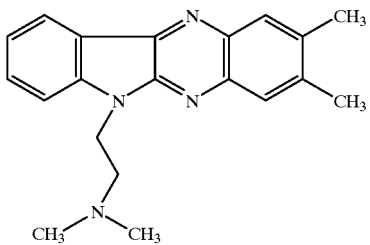

The EAE (experimental autoimmune encephalomyelitis) model is a generally accepted animal model for the acute MS symptoms ((1)Ruuls et al, J. Immunology, 1996, 157, 5721–5731; (2)van der Medide et al, J. Neuroimmunology, 1998, 84, 14–23; (3)Smith et al, Nature Medicine,2000, 6, 1, 62–66). The model is based on Lewis rats that day 0 are induced by 20 μg myeline peptide (MBP 68–86) och 2 mg of Myobacterium tuberculosis. After one week severe CNS symptoms appear that are by double blind examination given a value—a clinical score. The higher value, the more severe effect. The scale is 0–5. After some 14 days there is a peak in symptoms followed by a decline back to the normal situation.

Figure 1:
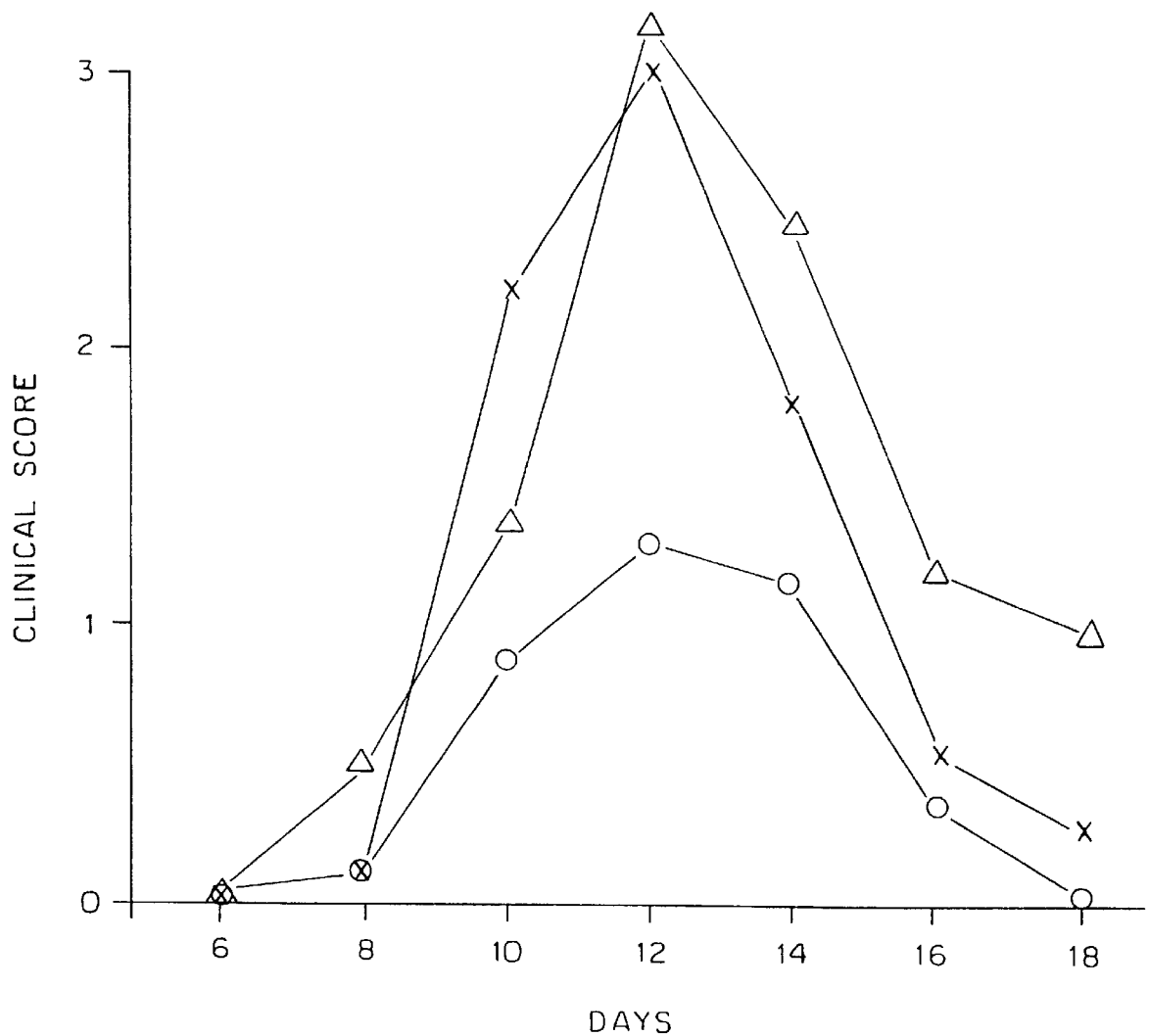
FIG. 1 shows the results obtained in an EAE model test.

The negative control has no treatment except the immunization (day 0) to induce the acute MS response. In FIG. 1 the results from the negative control, Interferon-beta and a compound used according to the present invention, 2,3-dimethyl(dimethylaminoethyl)-5H-indolo-(2,3-b) quinoxaline, (B-220) are shown. From the figure it can be seen that Interferon-beta has no reducing effect of the CNS symptoms The lower curve represents the tested substance used according to the present invention, which substance surprisingly and unexpectedly reduces the CNS symptoms with 2/3.

In the test Interferon-beta was administered daily with $3 \times 10^5$ U/animal which is a medium dose (2). The tested substance(B-220), was administered daily with 6 mg/animal, a dose that can be increased since the margin to toxic effects is wide and most likely further reduce the symptoms. It is to be noted that the acute toxicity of the tested substance used according to the present invention is low, which is exemplified with the following:

$LD_{50}$, oral, rat; >800 mg/kg bw
$LD_{50}$, intravenous, rat; >100 mg/kg bw
NOEL, intravenous, rat; 12.5 mg/kg bw
NOEL, cutaneous, rabbit; 200 mg/kg bw
(NOEL=No Observable Effect Level)

The chronic toxicity has been tested up to 270 days on mice and the substance has not induced toxicity, on the contrary the substance has protected the animals for different health effects.

Figure 2:
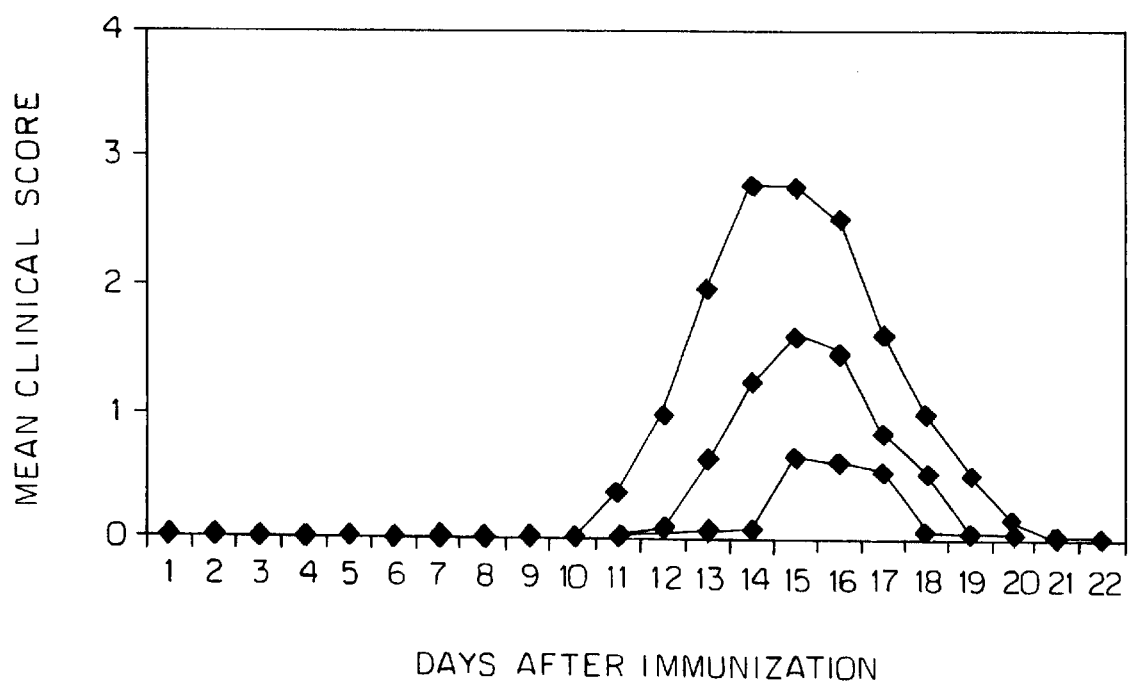
FIG. 2 shows the results obtained in an EAE rat model test with different doses of a compound used according to the present invention.

In the well established EAE rat model for multiple sclerosis (MS) a compound used according to the present invention, B-220, was shown to down-regulate the clinical symptoms (clinical score) in a dose dependent manner. The results are shown in FIG. 2. At the highest dose, 12 mg/animal, (lower curve) the onset is delayed approximate 4 days, the recovery starts approximate 3 days earlier and the total effect is dramatically lowered. A majority of the animals do not show any symptoms at all in this group. Symptom grading 1 is thus a very weak and mild effect while grading 3 is a severe paralysis. The intermediate curve illustrates a dose of 6 mg/animal and the onset is delayed approximate 2 days, the recovery starts approximate 2 days earlier and the total effect is substantially lower as compared to the control, highest curve, where no B-220 is added.

Figure 3:
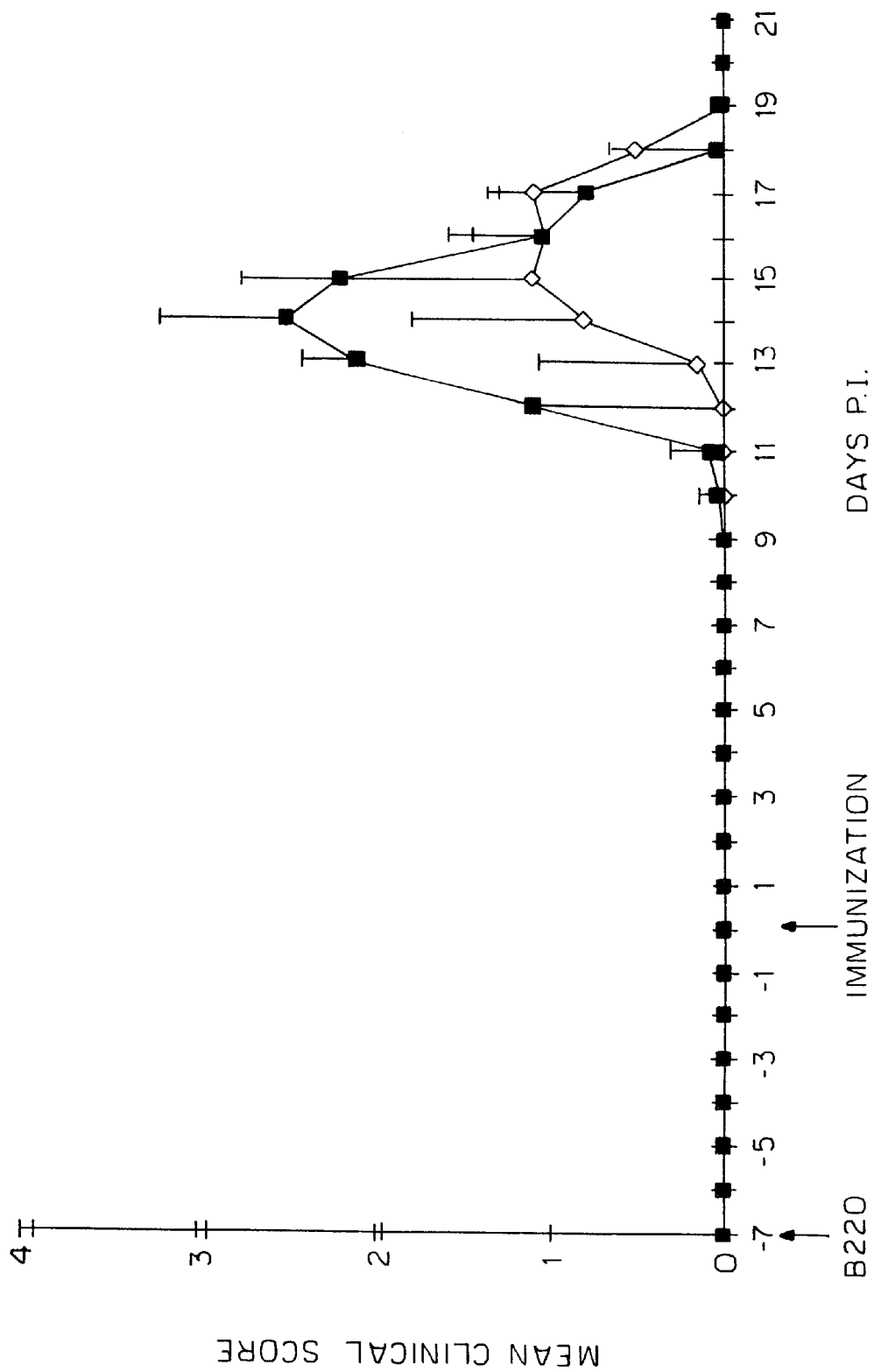
FIG. 3 shows the effect of pre-treatment with a compound used according to the present invention.

In FIG. 3 pre-treatment with B-220 before the onset of the disease is shown. The highest curve is illustrating the control without any added B-220 while the lower curve is after administration of B-220 of 6 mg/animal. As seen from the Figure the pre-treatment results in a clear lowered and delayed MS effect. Administration of B-220 was from −7 to +7 days in relation to the onset of disease (day 0).

Figure 4:
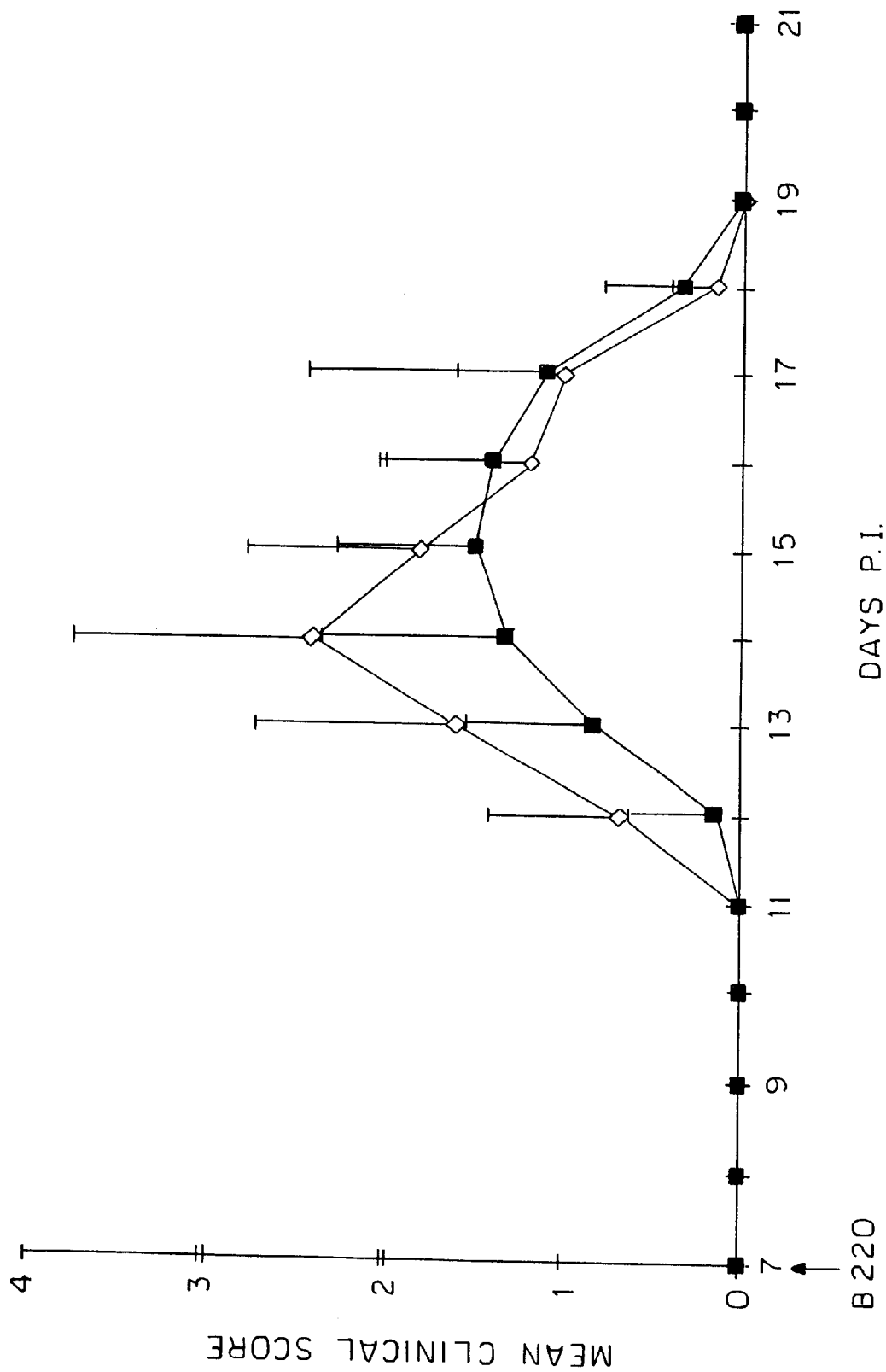
FIG. 4 shows the effect of after-treatment with a compound used according to the present invention.

In FIG. 4 after-treatment with B-220 starting from day 7 from the time point when the disease was initiated (day 0) and throughout the experiment is shown wherein the highest curve is a control without any addition of B-220 and the lower curve is representing a dose of 6 mg/animal of B-220. As seen from the Figure the after-treatment with B-220 lowered the MS effect in the rats.

The vertical lines in both FIG. 3 and FIG. 4 represent mean±standard deviation.

A suitable dosage range for humans is 1 to 50 mg/kg body weight.

What is claimed is:

1. A method for the treatment of multiple sclerosis comprising administering to a patient in need of said treatment an amount effective therefor of a compound of formula I:

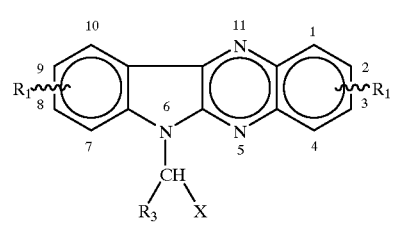

wherein $R_1$ represents hydrogen or one or several, preferably 1 to 4, similar or different substituents in the positions 1–4 and/or 7–10, selected from halogen, preferably Br, lower alkyl/alkoxy group having not more than 4 carbon atoms, trifluoromethyl group, trichloromethyl group; and in one of the positions 7–10 $R_1$ can be a hydroxyl group;

X is a group —$(CH_2)_n$—$R_2$, wherein $R_2$ represents a nitrogen containing basic residue such as $NH_2$, $NHR_4$ or $NR_5R_6$, wherein $R_4$, $R_5$ and $R_6$ independently are lower alkyl or cycloalkyl and n is an integer of from 1 to 4 and $R_3$ represents hydrogen, lower alkyl/cycloalkyl group having not more than 4 carbon atoms, or a physiologically acceptable addition product thereof with an acid or halogen adduct.

2. The method according to claim 1 wherein said compound is a physiologically acceptable addition product with an adduct of iodine, iodine monochloride or iodine monobromide.

3. The method of claim 1, wherein $R_1$ is methyl in positions 2 and 3 and hydrogen in the other positions, or a physiologically acceptable addition product thereof.

4. The method of claim 3, wherein $R_1$ in one of the positions 7–10 is hydroxy.

5. The method of claim 4, wherein $R_1$ in position 9 is hydroxy.

6. The method of claim 2, wherein $R_1$ in one of the positions 7–10 is hydroxy.

7. The method of claim 6, wherein $R_1$ in position 9 is hydroxy.

8. The method of claim 1, wherein $R_1$ in one of the positions 7–10 is hydroxy.

9. The method of claim 8, wherein $R_1$ in position 9 is hydroxy.

10. The method of claim 1 wherein X is $CH_2N(CH_3)_2$ and $R_3$ is hydrogen.

11. The method of claim 2 wherein X is $CH_2N(CH_3)_2$ and $R_3$ is hydrogen.

12. The method of claim 3 wherein X is $CH_2N(CH_3)_2$ and $R_3$ is hydrogen.

13. The method of claim 4 wherein X is $CH_2N(CH_3)_2$ and $R_3$ is hydrogen.

14. The method of claim 5 wherein X is $CH_2N(CH_3)_2$ and $R_3$ is hydrogen.

15. The method of claim 6 wherein X is $CH_2N(CH_3)_2$ and $R_3$ is hydrogen.

16. The method of claim 7 wherein X is $CH_2N(CH_3)_2$ and $R_3$ is hydrogen.

17. The method of claim 8 wherein X is $CH_2N(CH_3)_2$ and $R_3$ is hydrogen.

18. The method of claim 9 wherein X is $CH_2N(CH_3)_2$ and $R_3$ is hydrogen.

* * * * *